(12) United States Patent
Pelletier et al.

(10) Patent No.: US 7,412,777 B2
(45) Date of Patent: Aug. 19, 2008

(54) METHOD AND APPARATUS FOR CALIBRATING SPHERICAL OBJECTS USING A COMPUTER SYSTEM

(75) Inventors: Benoit Pelletier, Montreal (CA); Sébastien Jutras, Montreal (CA); Bruno Falardeau, Verdun (CA); Mathieu Légaré, St-Esprit (CA)

(73) Assignee: Orthosoft Inc., Montréal, Québec (CA)

( * ) Notice: Subject to any disclaimer, the term of this patent is extended or adjusted under 35 U.S.C. 154(b) by 41 days.

(21) Appl. No.: 11/434,786

(22) Filed: May 17, 2006

(65) Prior Publication Data

US 2006/0260147 A1    Nov. 23, 2006

Related U.S. Application Data

(60) Provisional application No. 60/682,852, filed on May 20, 2005.

(51) Int. Cl.
*G01B 5/20* (2006.01)
(52) U.S. Cl. ........................................................ 33/520
(58) Field of Classification Search .................. 33/520, 33/644, 549, 543, 550, 551, 552, 555
See application file for complete search history.

(56) References Cited

U.S. PATENT DOCUMENTS 3,766,653 A    10/1973    McKay
4,137,640 A *   2/1979    Parks ........................... 33/507
5,341,574 A     8/1994    Bieg
6,493,956 B1   12/2002    Matsuda
6,578,281 B2 *  6/2003    Takahashi .................. 33/555.1
6,820,347 B2 * 11/2004    Mellander ................. 33/555.1
7,024,785 B2 *  4/2006    Dall'Aglio et al. ......... 33/555.3

FOREIGN PATENT DOCUMENTS

| WO | 83-01999 | 6/1983 |
|----|----------|--------|
| WO | 03/038375 | 5/2003 |

* cited by examiner

*Primary Examiner*—Christopher W Fulton
(74) *Attorney, Agent, or Firm*—Ogilvy Renault LLP

(57) ABSTRACT

A method of determining a center of curvature of the spherical outer surface of an object using a computer system is provided. The method includes defining at least one contact region on the spherical outer surface in a plane substantially tangential to a circumference thereof and a first reference axis normal to said plane. Spatial coordinates of at least one of a first and a second geometric parameter are determined, the first geometric parameter including at least two points located on the spherical outer surface and the second geometric parameter including a second reference axis normal to the spherical outer surface. The center of curvature of the spherical outer surface is then calculated using the first reference axis and at least one of the first and second geometric parameters. An associated system and calibration device is also provided.

27 Claims, 7 Drawing Sheets

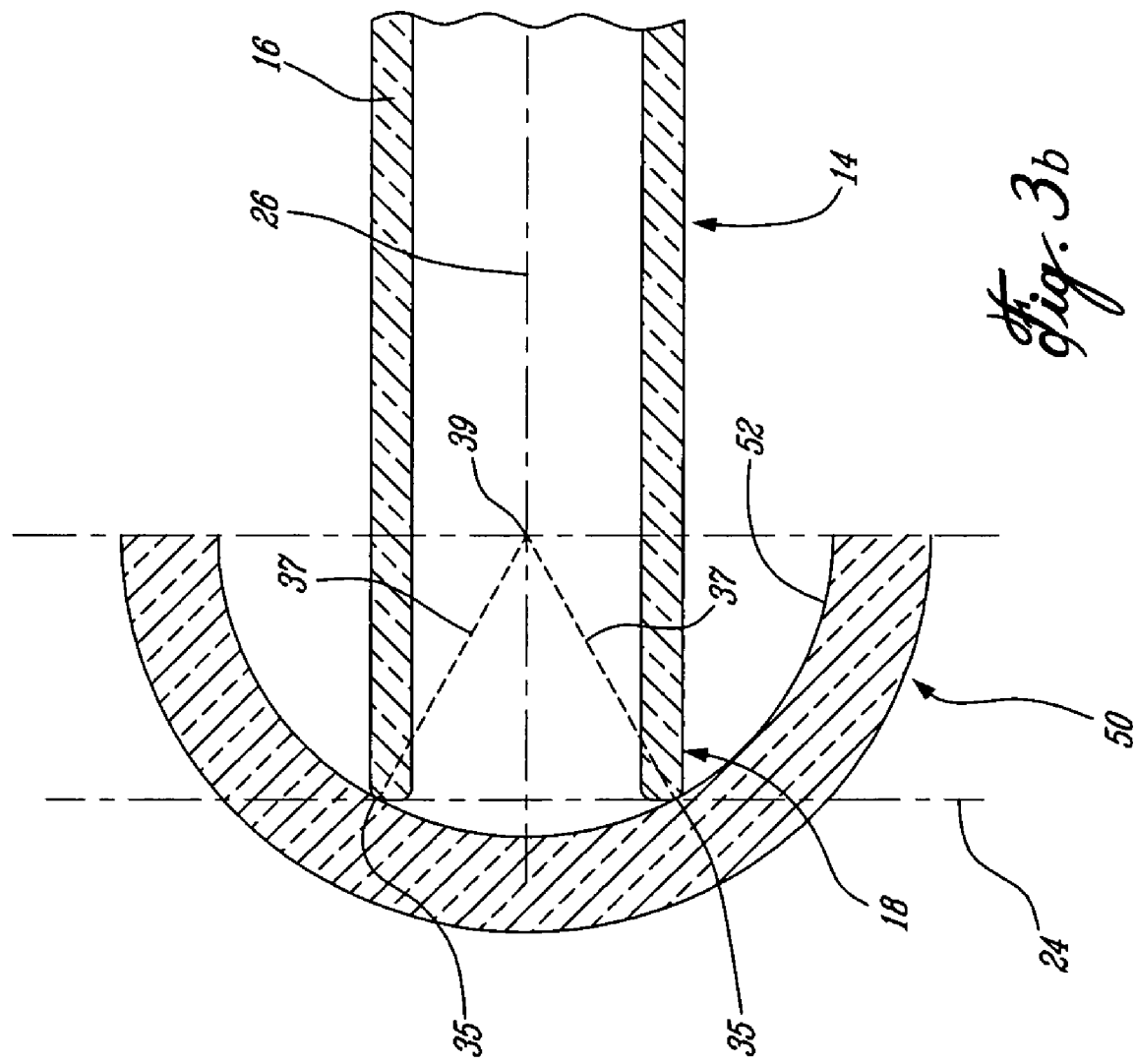

METHOD AND APPARATUS FOR CALIBRATING SPHERICAL OBJECTS USING A COMPUTER SYSTEM

CROSS-REFERENCE TO RELATED APPLICATIONS

This application claims priority on U.S. Provisional Patent Application Ser. No. 60/682,852 filed May 20, 2005, the entire contents of which is incorporated herein by reference.

TECHNICAL FIELD

The invention relates generally to a calibrating device for use in conjunction with a computer system, and more particularly to an improved method and apparatus for determining the center point of a spherical object.

BACKGROUND OF THE ART

Proper calibration of tools, bone structures, implants and other components used in computer assisted surgery (CAS) procedures is vital.

In particular, determining the center of rotation (COR) of a spherically shaped object for use during a CAS surgery is a fairly common, but nonetheless important procedure. For example, during a total hip replacement (THR) surgery, determining the COR of the partially spherical femoral head and/or the corresponding cup-shaped acetabulum within which it is received, is typically required in order to ensure proper relative positioning of the respective femoral head and acetabular cup implants.

At least two known methods are currently employed for determining the COR of such a spherical object using a CAS system. For simplicity, these methods will be briefly described with reference to calculating the center of rotation of a femoral head. The first method involves rotating the femur between several positions, and capturing position and orientation information at each of the positions using the CAS system, from which the CAS system is able to determine the center point about which the femur is rotating by extrapolating lines from each of the captured positions and determining an intersection point thereof. More specifically, the femur is first maintained in a stable position such that the CAS system is able to register its position in space. The femur is then rotated to another position, and the position capturing procedure is repeated. This is repeated in order to permit the CAS system to identify and capture at least three distinct positions of the femur, from which the CAS system can define and calculate an imaginary cone having a tip coincident with the COR of the femoral head about which the femur was rotated between measured positions. Alternately, another method involves gradually rotating the femur in space during which time the CAS system automatically collects position and orientation information of the femur at predetermined regular intervals. These methods are simple, however have certain drawbacks. Particularly, if only three points are captured, the error margin remains relatively high. However, capturing a plurality of points, while improving accuracy, can be overly time consuming. Additionally, if the surgeon or user is not careful to displace the limb through its full rotational envelope and the points are captured too close to each other (i.e. linearly or quasi-linearly), then the resulting cone calculated by the CAS system will be skewed and not representative of the true COR of the limb. Further, another disadvantage of this method is the fact that it requires the surgeon to hold and rotate the limb of the patient through a relatively large region above the operating table, which in certain cases can at the very least be quite awkward. Other possibility for errors exists with these methods. For example, any displacement of the femoral head within the acetabulum as it is rotated therewithin, additionally adds error to the calculation of the tip of the cone and therefore the calculated center of rotation can differ from the true center of rotation of the limb by a significant amount.

A second method which as been employed to determine the COR of a spherical object using a CAS system involves using a tracked pointer or digitizer to collect a number of points on the spherical surfaces itself. Given a sufficient number of points on the surface, the CAS system is then able to reconstruct or digitize the surface, from which it can calculate an estimated center of rotation thereof. This method, however, requires relatively complex calculations on the part of the CAS system and further can result in imprecise results caused by an imperfectly digitized surface. This method also requires that a plurality of points on the surface of the spherical surfaces be digitized in order to provide accurate results.

Accordingly, there remains nonetheless a need for an improved device and method for determining the center of rotation of a spherical object using a CAS system.

SUMMARY OF THE INVENTION

It is therefore an object of this invention to provide an improved method and apparatus for determining the center point of a special object using a computer system.

In one aspect, the present invention provides a method of determining at least a center of curvature of a spherical outer surface of an object, the method comprising the steps of: defining at least one contact region on said spherical outer surface in a plane substantially tangential to a circumference thereof and a first reference axis normal to said plane; determining spatial coordinates of at least one of a first and a second geometric parameter, the first geometric parameter including at least two points located on said spherical outer surface and the second geometric parameter including a second reference axis normal to said spherical outer surface; and calculating the center of curvature of said spherical outer surface using said first reference axis and at least one of said first and second geometric parameters.

In another aspect, the present invention provides a method of determining a center of rotation of an object using a computer system, the object having an at least partially spherical outer surface and a diameter, the method comprising: providing a calibration device having a tracking member thereon which is in communication with the computer system, the calibration device including a tubular tip portion having a remote end defining an annulus and a central longitudinal axis, said annulus having a known diameter and being located a known distance from said tracking member; locating and tracking the calibration device in three dimensional space using the computer system; abutting said annulus against said spherical outer surface of said object to define an annular contact region therebetween and a first reference axis defined by said central longitudinal axis, said annular contact region defining a plane tangential to a circumference of the spherical outer surface and normal to said first reference axis; determining the spatial coordinates of at least two points on said spherical outer surface within said annular contact region using the computer system; and calculating a center of rotation of said object using at least said two points and said first reference axis.

In another aspect, the present invention provides a system for determining a center of curvature of a spherical outer surface of an object, the system comprising: a computer system operable to locate and track in three dimensional space at least one tracking member communicable with the computer system; a calibration device having a tip portion defining a longitudinal axis and having one of said tracker members engaged thereto, said tip portion defining an object contacting element at a remote end thereof, said object contacting element being located a known distance from said tracking member such that the position and orientation of the object contacting element in three dimensional space is determined by the computer system; and a calculation module for calculating the center of curvature of the spherical outer surface using at least the determined position and orientation of the longitudinal axis and the object contacting element, the object contacting element being adapted to abut against the outer spherical surface in at least three points and such that said longitudinal axis is normal to said spherical outer surface.

There is also provided, in accordance with another aspect of the present invention, a calibration device for determining a center of curvature of a spherical outer surface of an object using a computer system, the calibration device comprising: a body having a tip portion defining at least one object contacting element at a remote end thereof, the tip portion defining a central longitudinal axis therethrough, the object contacting element of said tip portion defining a contact plane substantially orthogonal to said longitudinal axis when abutted against said spherical outer surface; a tracking member engaged to said body, the tracking member being locatable and trackable in three dimensional space by the computer system; and wherein the object contacting element and the central longitudinal axis of the tip portion are disposed in known locations relative to said tracking member to permit their position and orientation in three dimensional space to be determined by the computer system, such that spatial coordinates of at least two points on the spherical outer surface of the object and a reference axis normal to the spherical outer surface are determinable by the computer system when the object contacting element is abutted thereagainst.

Further details of these and other aspects of the present invention will be apparent from the detailed description and figures included below.

DESCRIPTION OF THE DRAWINGS

Reference is now made to the accompanying figures depicting aspects of the present invention, in which:

FIG. 3*b* is a partial cross-sectional view of a tip of the calibration device of FIG. 1, shown abutted against a concave inner surface of a spherical object;

DETAILED DESCRIPTION OF THE PREFERRED EMBODIMENTS

Computer assisted surgery (CAS) systems are capable of real time location and tracking of a plurality of discrete objects in a surgical field. A variety of systems are used, however most require the patient bone elements to be identified and registered to pre-operatively taken anatomical scans or intra-operatively taken images of the same bone elements. Therefore, by using trackable members which can be located and tracked in space by the CAS system, the surgeon is able to use the CAS system as an aid when conducting procedures on the identified bone element. In order to ensure accuracy and repeatability, all tracked tools, prosthetic implants, bone elements and or other surgical objects employed in conjunction with such a CAS system must therefore be precisely calibrated. Although the embodiments described below all relate to such as CAS system, it is to be understood that the calibration device and method of the present invention may be employed with a computer system used in alternate fields other than surgical ones. For example, other applications may benefit from being able to use a computer system capable of monitoring, in real time, the position and movement of objects which are identifiable by the computer system. For example, in various manufacturing industries, tracking members may be fixed to displacing machines, tools, workpieces and/or other objects used in the manufacturing process, such that the positions of these objects may be located and tracked by a corresponding computer system. Automobile manufacturing may also employ such a computer system to identify, locate and track objects during the production process. In any of such alternate applications, a spherical object which might be employed would need to be properly calibrated, particularly in order to determine the exact center thereof. As such, the calibration device, system and method of the present invention, although preferably used in surgical applications, can similarly be employed in environments such as those described above.

Figure 1:
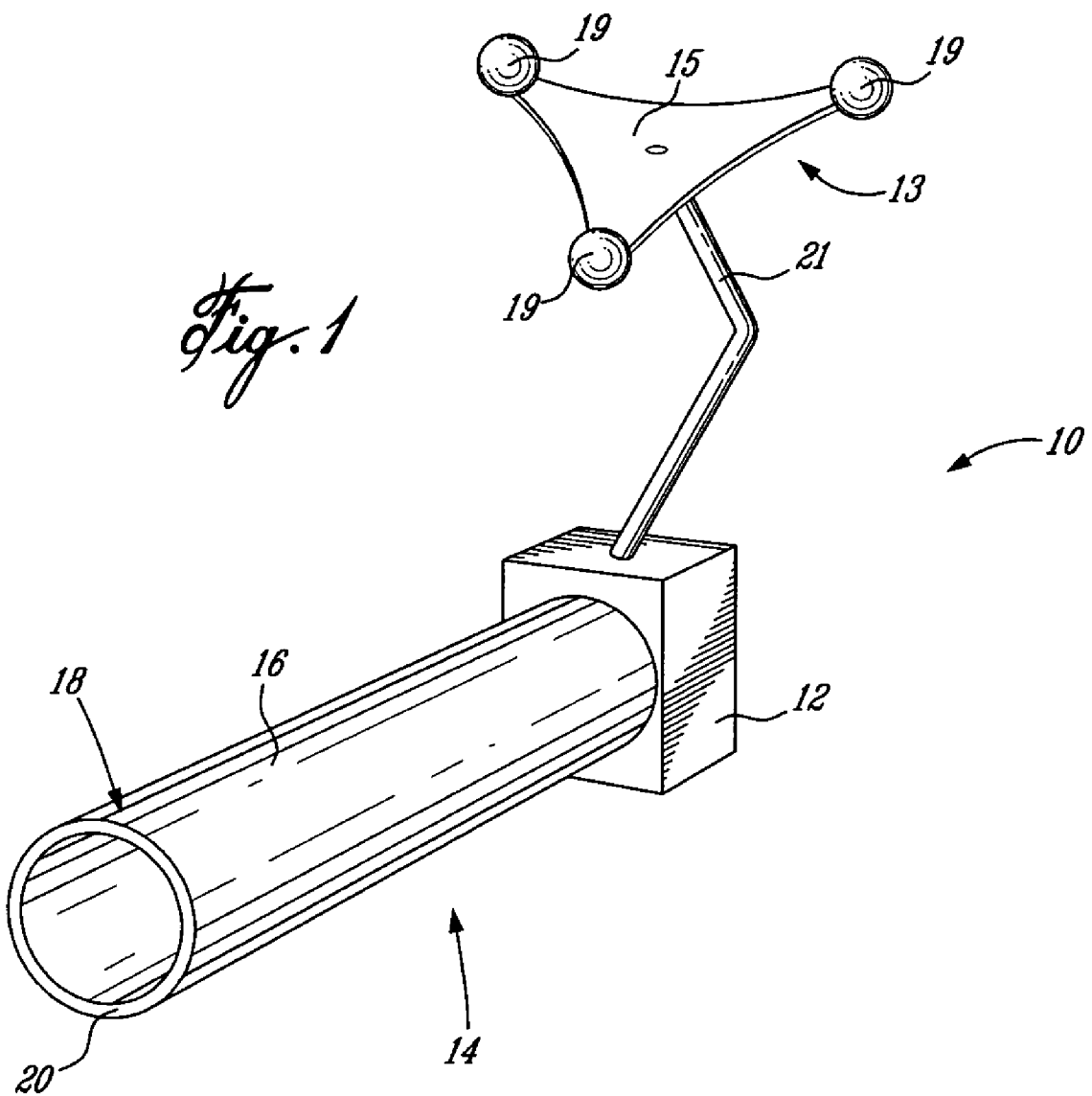
FIG. 1 is schematic perspective view of a calibration device, for use with a CAS system, in accordance with one embodiment of the present invention.
Figure 2:
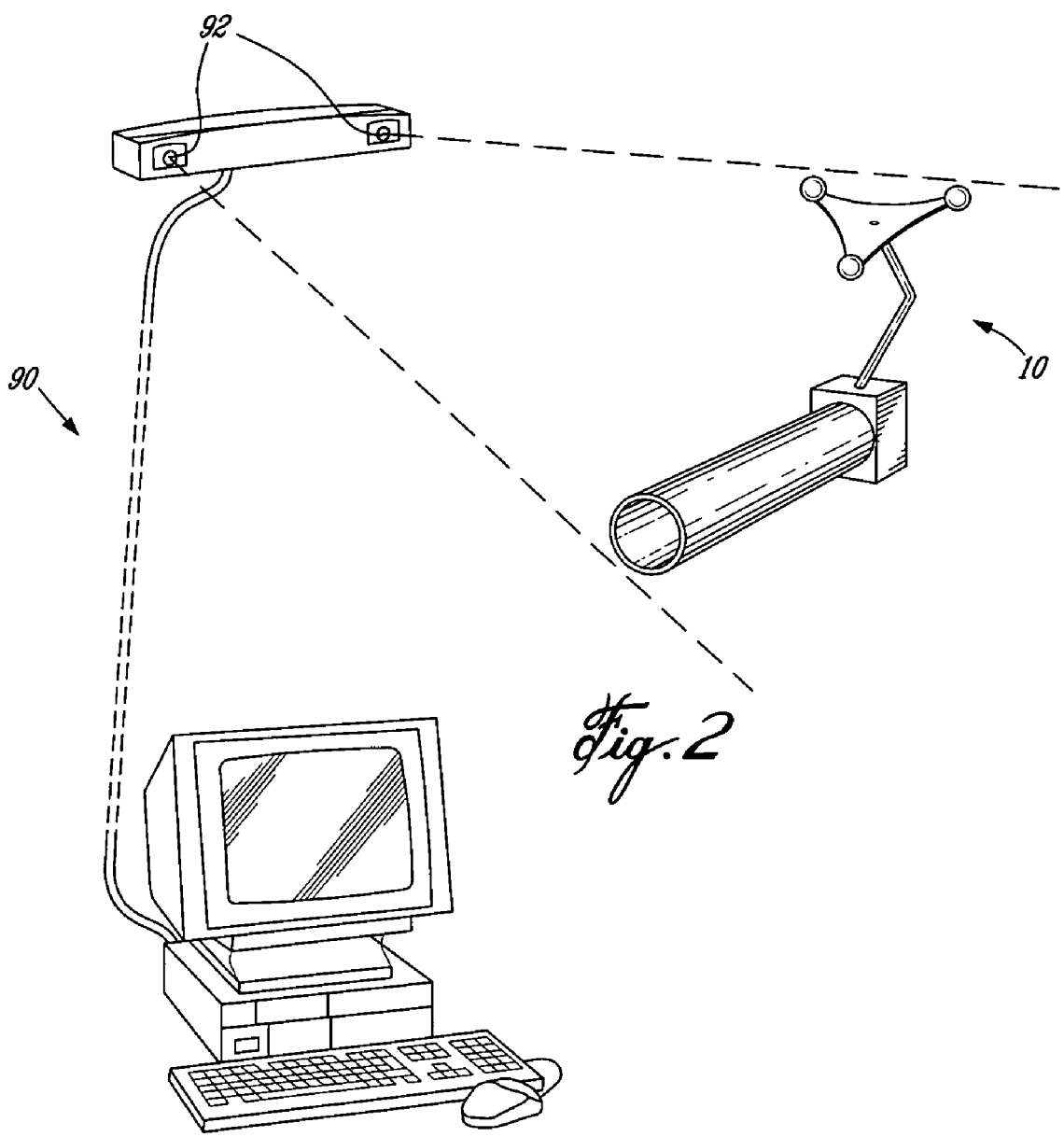
FIG. 2 is a schematic perspective view of the calibration device of FIG. 1 and the CAS system.

The calibration device 10 (FIG. 1) of the present invention is particularly adapted to be used with a computer assisted surgery (CAS) system 90, as schematically depicted in FIG. 2, in order to calibrate an at least partially spherical object.

The term "spherical object" as used herein is defined as an object having at least a portion thereof which is at least partially spherically shaped and therefore has either a concave and/or convex spherical surface and a center of curvature relative to the spherical surface. For example, such a spherical object can include a hollow hemispherical cup, a spherical ball, the head of a femur (whether natural bone or prosthetic implant), an acetabular cup (whether natural bone or prosthetic implant), and the like. Such objects may include circular, hemispherical, cup-shaped and other similar objects which comprise at least a curved or spherical outer surface having a center about which this surface is rotatable. The term "spherical object" used throughout is intended to include all such objects. These may include either portion of a ball and socket joint, whether bone or prosthetic implant. For example, the femoral head and/or the acetabulum within which it is received for rotation therewithin. Although both concave and convex spherical objects 40 (FIG. 3*a*), 50 (FIG. 3*b*) are schematically depicted herein as a perfect sphere and cup respectively, it is to be understood that these represent other spherical or at least partially spherical objects as identified above. In the embodiment described in detail herein, the spherical object is used in conjunction with a CAS system which permits the center thereof, and therefore the center of rotation of the object in three dimensional space, to be determined. The term "center of rotation" as used herein is intended to include a center of curvature of the spherical surface of the object, whether or not rotation of the object itself, or a mating/correspond element, occurs about this point.

Referring now to FIG. 1, the calibration device 10 is preferably a relatively small, hand held CAS calibrator which permits the instant determination of a spherical object's center of rotation. The calibration device 10 comprises generally a main body 12 and at least a tip portion 14 fastened to the main body 12 and projecting therefrom. The tip portion 14 may be either permanently fixed to the main body 12, or alternately detachable therefrom such that once the tip portion 14 has been used on a patient, it may be either disposed of and replaced with a new tip portion or cleaned and replaced for subsequent use. It is to be understood that the main body portion 12 may be relatively larger than the tip portion 14, or vice versa as depicted in FIG. 1. In one embodiment, the tip portion 14 is formed of a hollow cylindrical tube 16, the remote end 18 of which may define an annulus 20. Although the tip portion 14 is depicted in FIG. 1 as being a significant length relative to the main body portion 12, it is to be understood that the main body 12 can be much larger, longer, etc. than the tip portion 14, wherein the tip portion 14 is relatively smaller tubular tip at one end thereof. Further, although the tip portion 14 has an object contacting element at its remote end that is tubular in the first embodiment described herein, alternate configurations of this remote tip end are similarly possible, provided they comprise an object contacting element at the tip thereof for abutment against a spherical surface of the object to be calibrated. Such alternate tip portion configurations may include, for example, a solid cylinder with a concave tip, a ring spaced from but fastened to the main body of the calibration device, and a tubular tip element without a full annulus at the remote end thereof. Two other alternate embodiments of the tip portion of the calibration device of the present invention are also described in more detail below with reference to FIGS. 5 and 6.

A tracking member 13, which is located and tracked in three dimensional space by the CAS system 90 (as depicted in FIG. 2) used in conjunction with the calibration device 10, is fixed to the main body 12 of the calibration device 10 by a projecting support rod 21. The tracking member 13 generally comprises a tracker head element 15, preferably having three detectable element (i.e. CAS identification markers) 19 engaged, preferably removably, thereto. Each identification marker or detectable element 19 is identifiable by the CAS system employed, such that the three detectable elements 19 identify the location and orientation of the tracking member 13, and therefore the rest of the calibration device to which the tracking member 13 is fixed, in space. The detectable elements 19 are preferably optically detectable spheres, preferably coated with a retro-reflective layer, which are visible by, for example, at least two cameras and/or infrared sensors 92 of the optically-based CAS system 90. The cameras/sensors 92 of the CAS system 90 can therefore detect the position of each optically detectable sphere 19 illuminated by infrared light. Each detectable marker element 19 can alternately be any other type of position indicator such as a light emitting diode (LED) or a detectable electromagnetic indicator, provided each can be detected by the type of sensor used by the specific CAS system. Although the present calibration device 10 is most preferably adapted for use with an optically based CAS system 90, one skilled in the art will appreciate that in addition to the optical system mentioned above, other types of CAS tracking systems can equivalently be used, such as, for example, those which use electromagnetic, ultrasound or laser as a means for position identification. In such cases, it is to be understood that the detectable marker elements 19 will be such that they are able to indicate to, and/or be detected by, the particular CAS system used.

The annulus 20 defined by the remote tip end 18 of the tip portion 14 depicted is adapted to be abutted directly against an outer spherical surface of the spherical object for which the center is to be determined, as described in further detail below. As the tip portion is fixed in place to the main body 12 of the calibration device 10, the annulus 20 at the remote tip 18 of the tip portion 14 is therefore disposed in a known location relative to the tracking member 13 fixed to the main body 12. The inside and outside diameters of the tube 16 of the tip portion 14 are also known, as is the location of the central longitudinal axis 26 thereof. Although the annulus 20 depicted has slightly rounded edges, the tip 18 can also define an annulus which has non-rounded edges (i.e. wherein the outer surface of the tube 16 and the flat end surface of the annulus 20 meet at right angles).

Although preferably the remote tip end 18 and the annulus 20 formed thereon is of a fixed diameter and is fixed in place and immovable relative to the main body 12 of the calibration device 10, it remains possible that the remote tip end 18 is displaceable, such as to pivot relative to the main body 12 via an articulated joint therebetween or alternately to expand and/or contract such that the diameter of the annulus 20 is variable in order to be able to accept spherical objects of varying sizes for example. However, if the remote tip end 18 is displaceable relative to the tracking member 13 or has a variable diameter, the relative position between the tracking member 13 and the remote tip end 18, and therefore the annulus 20 formed thereby, as well as the adjusted diameter of the annulus 20 must be able to be determined by the CAS system 90 or identified thereto manually by a user.

Figure 3A:
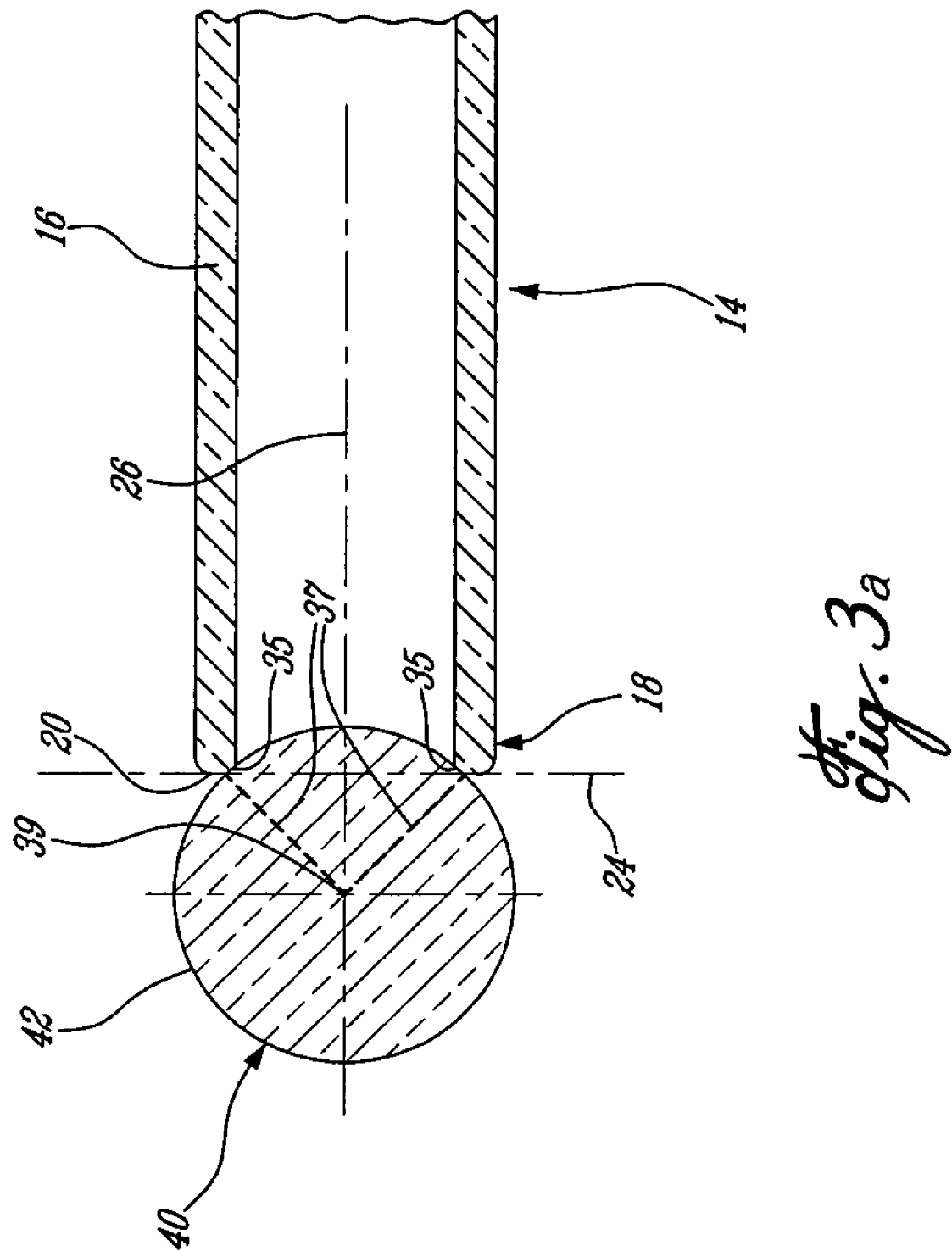
FIG. 3*a* is a partial cross-sectional view of a tip of the calibration device of FIG. 1, shown abutted against a convex outer surface of a spherical object.

The method of determining the center of rotation of a spherical object using the calibration device 10 will now be described with reference to FIGS. 3a-3b. The use of the calibration device 10 with the CAS system 90 (FIG. 2) permits the determination of the center of rotation of the spherical object, whether the diameter of the spherical surface of the object is known or unknown.

A first method is used when the diameter of the spherical surface of the object is known, or at least predetermined prior to calibrating the spherical object using the calibration device 10 and the CAS system 90. As depicted in FIGS. 3a-3b, the remote end 18 of the tube 16 which comprises the tip portion 14 of the calibration device 10 is abutted directly against the spherical surface of the spherical object to be calibrated, such that the annulus 20 defined at the remote tip end 18 mates with the spherical object about an annular contact region therebetween. In FIG. 3a, the spherical object 40 is a convex sphere (representing for example a femoral head) which comprises an outer spherical surface 42 against which the annulus 20 at the remote end 18 of the tubular tip portion is directly abutted. In FIG. 3b, the spherical object 50 is a concave cup (representing for example an acetabular socket) defining an inner concave spherical surface 52 therewithin, against which the remote end 18 of the tubular tip portion 14 is abutted to ensure an annular contact region therebetween. It is to be understood that when the spherical object being calibrated is a bone element of a patient, such as a femoral head or acetabulum for example, this bone element is separately tracked by the CAS using a bone tracking member fastened thereto (but not shown).

When the remote end 18 of the tubular tip portion 14, the location of which is known by the CAS system, is placed against one of the spherical surfaces 42/52, the annulus 20 at the tip end 18 in contact with the spherical surface 42/52 defines an imaginary plane 24 which is tangential to the circumference of the spherical surface 42/52 and substantially orthogonal to the longitudinal axis 26 of the tube 16 which at least partially comprises the tip portion 14. At least one contact point 35, between the spherical surface 42/52 and the annular tip 20 of the calibration device within the annular contact region therebetween, is captured be identified by the CAS system in a single reading. As the diameter of the spherical object 40/50 is known, the CAS system is able to determine the location of the center of rotation (COR) 39 of the spherical object, which lies along the known central longitudinal axis 26 at a distance away from the spherical surface 42/52 equal to the predetermined radius of the object. Thus, the exact location of the COR 39 is able to be determined by the CAS system. In an alternate means of calculating the COR, the CAS system is able to extrapolate an imaginary line 37 originating at each of at least one point 35 identified on the surface 42/52 and having a length equal to the known radius (i.e. half the known diameter) of the spherical surface 42/52. The lines 37 intersect one another and the longitudinal axis 26 of the tubular tip portion 14 at a single point 39. This intersection point 39 defines the COR of the spherical object being calibrated. The CAS system is thus able to determine the location in space of this COR point 39 of the spherical object.

Accordingly, the calibration device 10 may be used with the CAS system 90 in order to simply and quickly determine the COR of almost any spherical object (whether concave or convex), by merely abutting the end 18 of the tip portion 14 once (i.e. for a single reading) against the spherical surface, and acquiring points using the CAS system. Further, due to the annular shape of the tubular tip portion of the calibration device, when abutted against a spherical surface the center of rotation of the surface is self-centered in alignment with the known longitudinal axis 26 of the tubular portion 16 of the device.

Figure 4B:
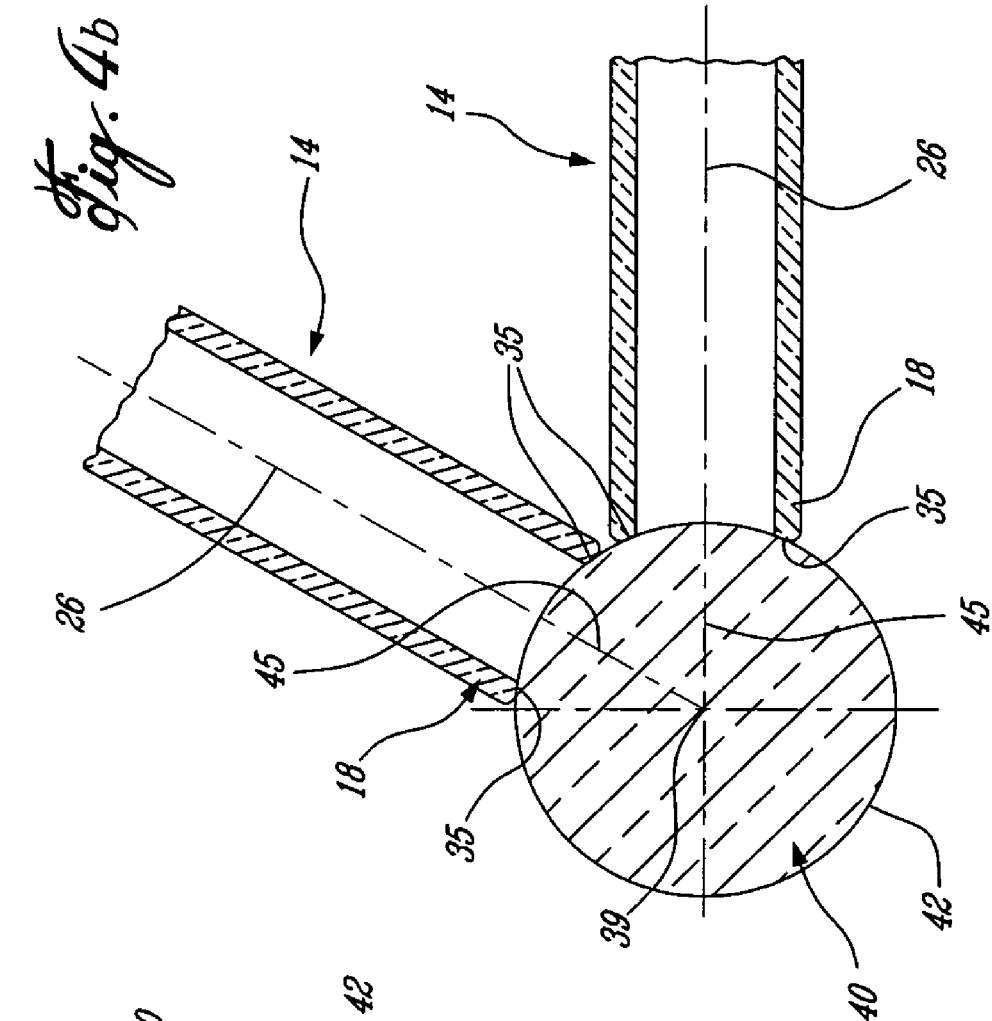
FIG. 4*b* is a partial cross-sectional view of the calibration device and spherical object of FIG. 4*a*.
Figure 4A:
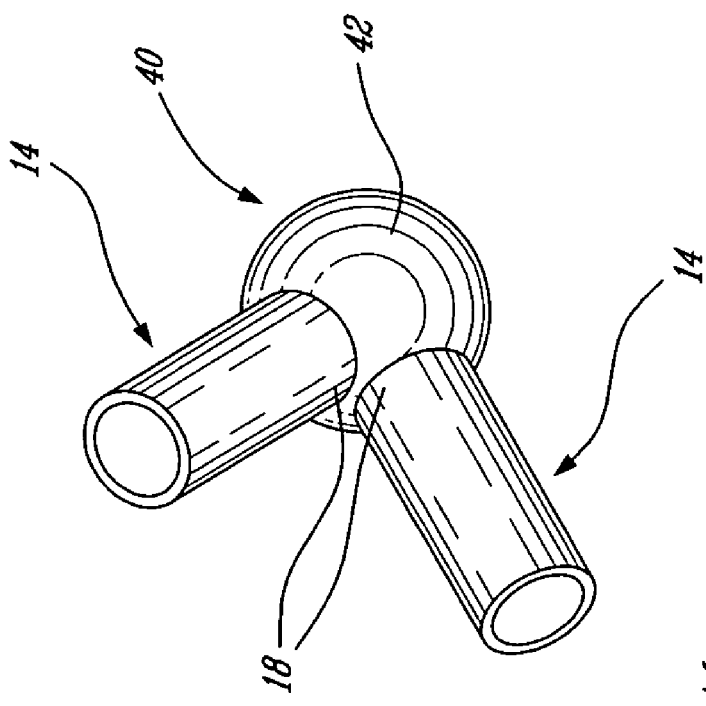
FIG. 4*a* is a schematic view of a tip portion of the calibration device of FIG. 1 shown for demonstration purposes simultaneously in two locations on a spherical object, in accordance with an alternate method of the present invention.

A second method in accordance with another embodiment of the present invention, as depicted in FIG. 4a-4b, is used when the diameter of the spherical object being calibrated is unknown. The same calibration device 10 is employed, and the method is similar to that described above when the diameter of the spherical object is known, this second method however involves an additional step. Namely, once the annular remote end 18 of the tubular tip portion 14 has been abutted a first time against the spherical outer surface 42 of the convex spherical object 40 as described above (i.e. in a first position) in order to capture points on the spherical surface in a first reading, the calibration device 10 is then displaced by the user and abutted a second time in a different position (i.e. a second position) against another region of the spherical surface 42 for a second reading by the CAS system. (The tubular tip portion 14 of the calibration device 10 is depicted for ease of explanation in both the first and second positions in FIG. 4a-4b, however only one calibration device is used for both readings.) In each position of the calibration device 10, the CAS system determines the positional information of the annular tip 18 thereof, and therefore points in the annular contact region on the outer surface 42. Thus, at each of the first and second positions, a reference line 45 is defined which is collinear with the longitudinal axis 26 of the tubular tip portion 14 of the calibration device 10. Each of these two reference lines 45 interests in space at a single point 39 which defines the center of rotation of the spherical object. The CAS system can therefore calculate the diameter of the spherical object being calibrated, using trigonometry as the location of the abutment points 35 between the tip 18 and the surface 42 and the determined center of rotation 39.

Therefore, the calibration device, when used in accordance with the methods described above 10 and the CAS system 90, permits the quick and easy determination of the center of rotation of a spherical object for subsequent use in a computer assisted surgical procedure.

Figure 5:
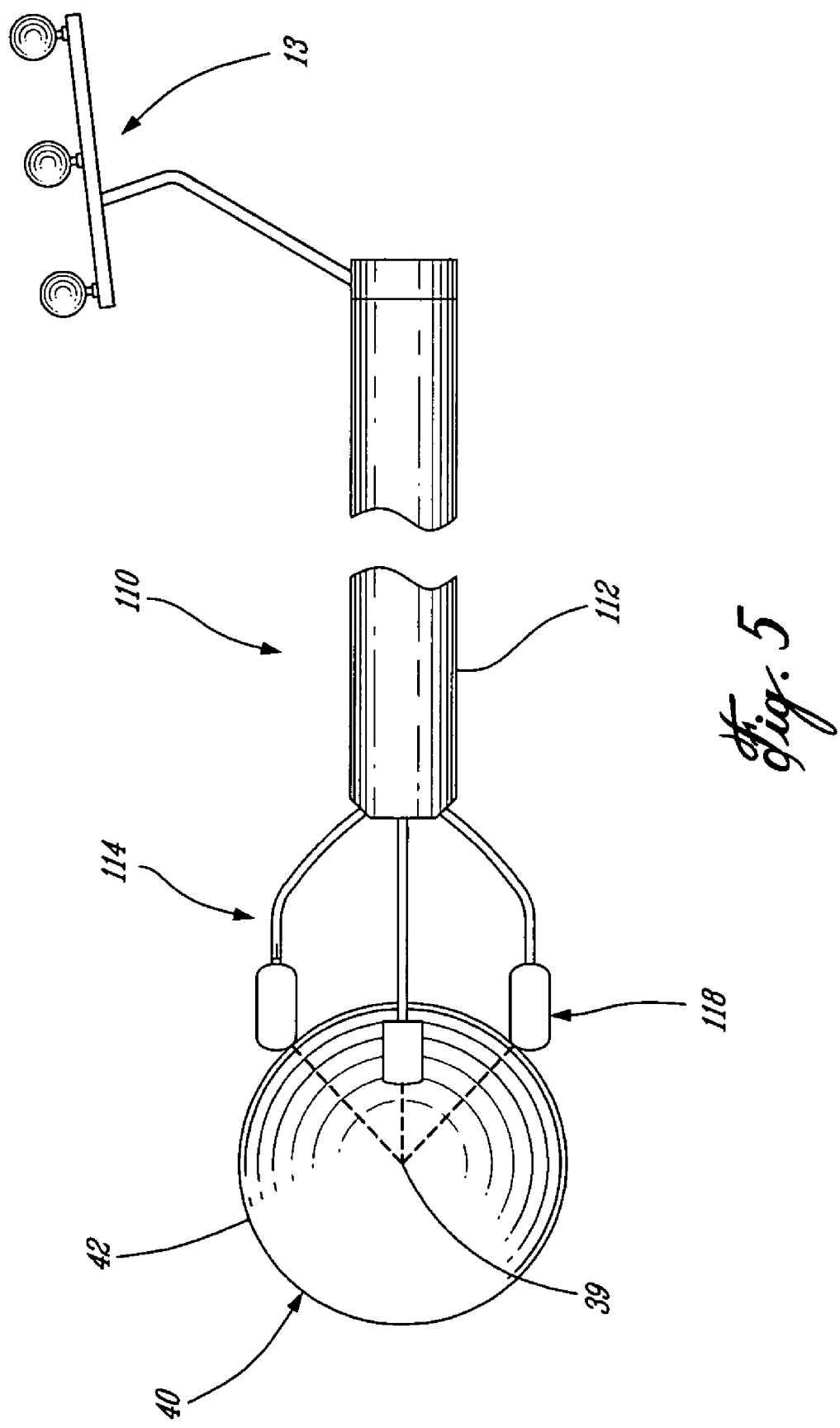
FIG. 5 is a side elevation view of a calibration device in accordance with an alternate embodiment of the present invention.
Figure 6:
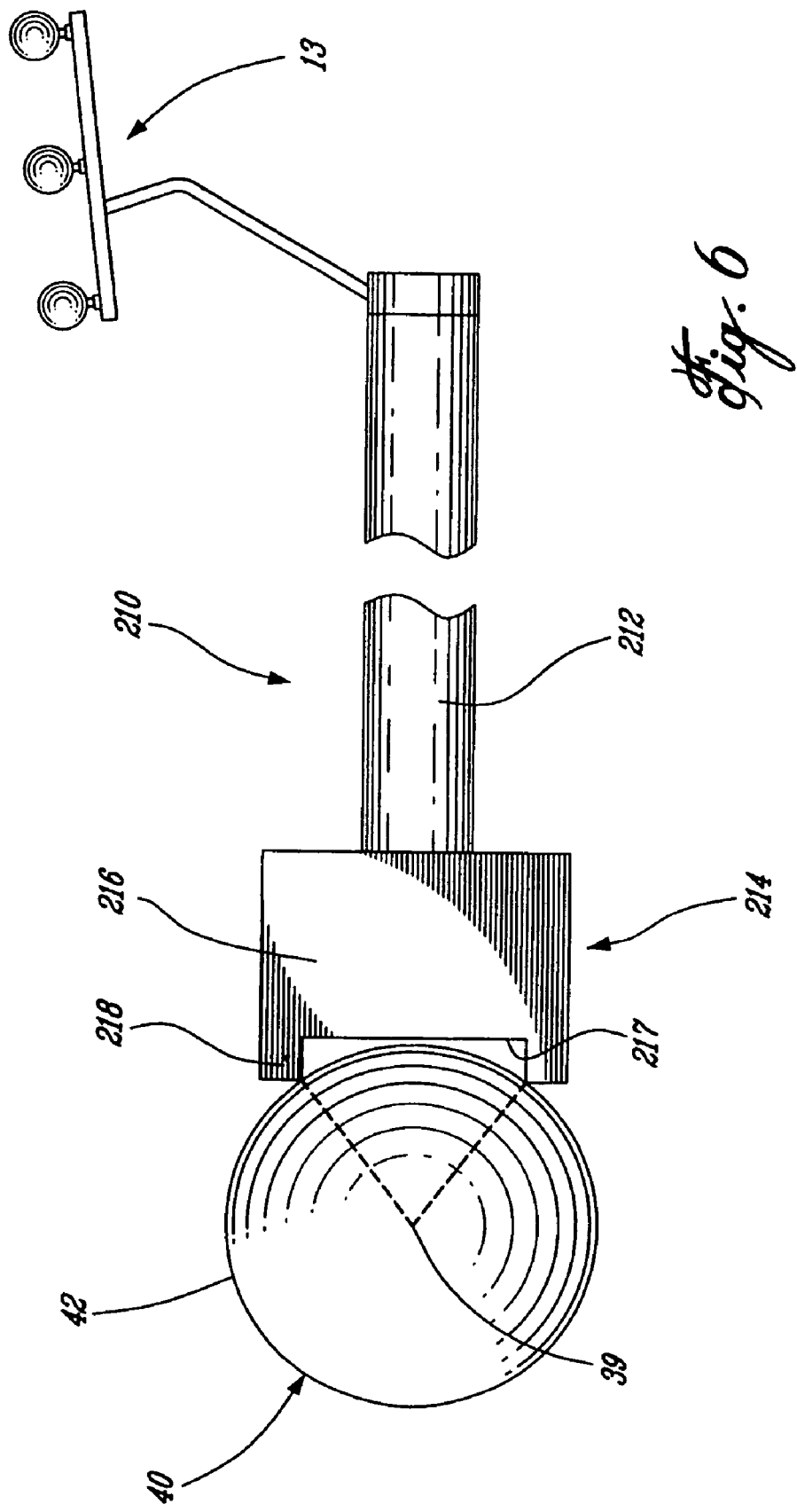
FIG. 6 is a side elevation view of a calibration device in accordance with another embodiment of the present invention.

Referring to FIGS. 5 and 6, two alternate embodiments of the tip portion of the calibration device of the present invention are depicted. In FIG. 5, the calibration device 110 comprises a main body 112, defining a handle portion, and having a tracking member 13 fastened thereto. The tip portion 114 of the calibration device 110 comprises an object contacting element that includes at least three projecting individual fingers or tip ends 118, which are preferably evenly angularly spaced apart. Each tip end 118 is adapted to abut the spherical object 40 at distinct points on the spherical surface 42 thereof. Therefore, much as the annulus 20 of the tip portion 14, the individual tip ends 118 abut the spherical surface within an annular region therearound, however only at three discrete points. The position of the these three points abutted by the tip ends 118 is captured by the CAS system in a single reading, in order to determine the location of the center of the spherical object (when the diameter thereof is known). As described above, when the diameter is unknown, the tip ends 118 must be displace such that a second reading may be taken. In FIG. 6, the calibration device 210 comprises a main body 212, which may define a handle portion, to which is fastened the tracking member 13. The tip portion 214 of the calibration device 210 comprises an object contacting element having a structure 216 defining at least three notches 217 at the remote end 218 thereof. (Only one such notch 217 is visible in FIG. 5.) These notches 217 act much as the fingers or tip ends 118, wherein the edges at the remote end tips 218 abutting the outer spherical surface 42 of the spherical object 40. The tip portions 114 and 214 act and are operable much as per the tip portion 14 described above, in order to determine the center of the spherical object being calibrated by the calibration device.

The above description is meant to be exemplary only, and one skilled in the art will recognize that changes may be made to the embodiments described without department from the scope of the invention disclosed. Still other modifications which fall within the scope of the present invention will be apparent to those skilled in the art, in light of a review of this disclosure, and such modifications are intended to fall within the appended claims.

The invention claimed is:

1. A method of determining at least a center of curvature of a spherical outer surface of an object, the method comprising the steps of:
    defining an annular contact region on said spherical outer surface in a contact plane that is parallel to a plane tangential to a circumference thereof and a first reference axis normal to said contact plane, said first reference axis being located at a center of said annular contact region;
    determining spatial coordinates of at least one of a first and a second geometric parameter, the first geometric parameter including at least two points located on said spherical outer surface and the second geometric parameter including a second reference axis normal to said spherical outer surface;

calculating the center of curvature of said spherical outer surface using said first reference axis and at least one of said first and second geometric parameters; and providing a computer system operable to locate and track pre-identified objects in three dimensional space, and using the computer system to perform at least said steps of determining and calculating.

2. The method as defined in claim 1, wherein the step of determining said first geometric parameter comprises defining said at least two points on said spherical outer surface within said contact region.

3. The method as defined in claim 1, wherein the step of calculating comprises using said first reference axis and said first geometric parameter when a radius of the spherical outer surface is known.

4. The method as defined in claim 3, wherein the step of calculating further comprises extrapolating at least two imaginary lines having a length equal to said radius and extending from said at least two points on said spherical outer surface, said center of curvature being located at an intersection of said two imaginary lines and said first reference axis.

5. The method as defined in claim 1, wherein the step of defining comprises providing a calibration device having a tubular tip defining a central longitudinal axis and a remote annular end of a known diameter, and abutting said remote annular end against said spherical outer surface in at least one location thereon, said contact region being defined by that portion of the spherical outer surface in contact with said remote annular end, said central longitudinal axis of said tubular tip defining said first reference axis.

6. The method as defined in claim 1, further comprising a step of calculating a third geometrical parameter representative of the radius of curvature of the spherical outer surface.

7. The method as defined in claim 6, wherein the step of calculating the third geometric parameter further comprises calculating a distance between at least one point located on the spherical outer surface and the calculated center of curvature thereof.

8. The method as defined in claim 1, wherein the step of calculating comprises using said first reference axis and said second geometric parameter when a radius of the spherical outer surface is unknown.

9. The method as defined in claim 8, further comprising determining an intersection point between said first reference axis and said second reference axis, said intersection point corresponding to said center of curvature.

10. The method as defined in claim 1, wherein the step of defining further comprises defining a second contact region on said spherical outer surface, said second reference axis being located at a center of said second contact region.

11. The method as defined in claim 10, further comprising providing a calibration device having a tubular tip defining a central longitudinal axis and a remote annular end, and abutting said remote annular end against said spherical outer surface in at least two different locations to respectively determine said contact region and said second contact region defined by portions of the spherical outer surface in contact with said remote annular end, said contact region and said second contact region being annular, said central longitudinal axis of said tubular tip defining said first reference axis and said second reference axis respectively within said contact region and said second contact region.

12. The method as defined in claim 1, wherein the computer system is a computer assisted surgery system, further comprising using the computer assisted surgery system to perform at least said steps of determining and calculating.

13. A method of determining a center of rotation of an object using a computer system, the object having an at least partially spherical outer surface and a diameter, the method comprising:

providing a calibration device having a tracking member thereon which is in communication with the computer system, the calibration device including a tubular tip portion having a remote end defining an annulus and a central longitudinal axis, said annulus having a known diameter and being located a known distance from said tracking member;

locating and tracking the calibration device in three dimensional space using the computer system;

abutting said annulus against said spherical outer surface of said object to define an annular contact region therebetween and a first reference axis defined by said central longitudinal axis, said annular contact region defining a contact plane that is parallel to a plane tangential to a circumference of the spherical outer surface and normal to said first reference axis;

determining the spatial coordinates of at least two points on said spherical outer surface within said annular contact region using the computer system; and calculating a center of rotation of said object using at least said two points and said first reference axis.

14. The method as defined in claim 13, wherein the step of calculating includes using a known geometric parameter of the object representative of a radius thereof.

15. The method as defined in claim 14, the step of calculating further comprises extrapolating at least two imaginary lines having a length equal to said radius and extending from said at least two points on said spherical outer surface, and determining an intersection point of said two imaginary lines and said first reference axis, said intersection point corresponding to said center of rotation.

16. The method as defined in claim 13, further comprising determining a geometric parameter representative of a radius of the object by calculating a distance between at least one of said at least two points identified on said spherical outer surface and the calculated center of rotation.

17. The method as defined in claim 13, further comprising abutting said annulus against a second region of said spherical outer surface, and using the computer system to determine an intersection point between said first reference axis and a second reference axis collinear with the central longitudinal axis of the tubular tip portion when abutted against said second region, wherein said intersection point defines the center of rotation of the object.

18. A system for determining a center of curvature of a spherical outer surface of an object, the system comprising:

a computer system operable to locate and track in three dimensional space at least one tracking member communicable with the computer system;

a calibration device having a tip portion defining a longitudinal axis and having one of said tracker members engaged thereto, said tip portion defining an object contacting element at a remote end thereof, said object contacting element being located a known distance from said tracking member such that the position and orientation of the object contacting element in three dimensional space is determined by the computer system, said object contacting element including at least three contact points which define a contact plane substantially orthogonal to said longitudinal axis; and a calculation module for calculating the center of curvature of the spherical outer surface using at least the determined position and orientation of the longitudinal axis and the object contacting element, the object contacting element being adapted to abut against the outer spherical surface in at least three points and such that said longitudinal axis is normal to said spherical outer surface.

19. The system as defined in claim 18, wherein the tip portion of the calibration device is tubular, the central longitudinal axis being defined centrally therethrough, and the object contacting element including an annulus for abutting against said spherical outer surface, said at least three contact points being defined on the annulus.

20. The system as defined in claim 18, wherein the object contacting element includes one of a discrete finger tip, a notched tip and a partial ring tip.

21. The system as defined in claim 18, wherein the computer system is a computer assisted surgery system.

22. The system as defined in claim 21, comprising an output device for displaying said determined center of curvature.

23. The system as defined in claim 22, wherein a relative position of the center of curvature is graphically displayed relative to said object on said output device.

24. A calibration device for determining a center of curvature of a spherical outer surface of an object using a computer system, the calibration device comprising:
   a body having a tip portion defining at least one object contacting element at a remote end thereof, the tip portion defining a central longitudinal axis therethrough, the object contacting element of said tip portion defining a contact plane substantially orthogonal to said longitudinal axis when abutted against said spherical outer surface;
   a tracking member engaged to said body, the tracking member being locatable and trackable in three dimensional space by the computer system; and
   wherein the object contacting element and the central longitudinal axis of the tip portion are disposed in known locations relative to said tracking member to permit their position and orientation in three dimensional space to be determined by the computer system, such that spatial coordinates of at least two points on the spherical outer surface of the object and a reference axis normal to the spherical outer surface are determinable by the computer system when the object contacting element is abutted thereagainst.

25. The calibration device as defined in claim 24, wherein the tip portion is tubular, and said object contacting element is an annulus defined at the remote end thereof.

26. The calibration device as defined in claim 24, wherein the object contacting element includes at least three points of contact with the spherical outer surface.

27. The calibration device as defined in claim 26, wherein the object contacting element includes one of a discrete finger tip, a notched tip and a partial ring tip, each of which having said at least three points of contact which lie within said contact plane.

* * * * *